United States Patent [19]
Nakamura

[11] Patent Number: 5,818,638
[45] Date of Patent: Oct. 6, 1998

[54] DEFLECTION COMPENSATING STRUCTURE FOR MEDICAL STAND APPARATUS

[75] Inventor: Katsushige Nakamura, Tokyo, Japan

[73] Assignee: Mitaka Kohki Co. Ltd., Tokyo, Japan

[21] Appl. No.: 753,596

[22] Filed: Nov. 27, 1996

[51] Int. Cl.⁶ ............................... G02B 21/00; A47F 5/00
[52] U.S. Cl. ................. 359/384; 248/123.2; 248/281.11
[58] Field of Search .................... 359/382, 383, 359/384; 248/123.11, 123.2, 280.11, 281.11

[56] References Cited

U.S. PATENT DOCUMENTS

| | | | |
|---|---|---|---|
| 4,339,100 | 7/1982 | Heller | 248/123.1 |
| 4,741,607 | 5/1988 | Heller | 359/384 |
| 4,881,709 | 11/1989 | Nakamura | 248/281.1 |
| 4,961,636 | 10/1990 | Gaul et al. | 359/381 |
| 5,173,802 | 12/1992 | Heller | 359/384 |
| 5,205,522 | 4/1993 | Nakamura | 248/123.1 |
| 5,480,114 | 1/1996 | Nakamura | 248/123.2 |
| 5,528,417 | 6/1996 | Nakamura | 359/384 |

Primary Examiner—Paul M. Dzierzynski
Assistant Examiner—Mark A. Robinson
Attorney, Agent, or Firm—Michael D. Bednarek; Kilpatrick Stockton LLP

[57] ABSTRACT

A compensating arm is provided extending from the proximal end at a joint to the distal end of a jib arm and arranged identical in the horizontal length to the jib arm. The compensating arm is pivotally joined at its distal end to the distal end of the jib arm and at its proximal end fixedly joined to a pivot which extends across the joint of the jib arm, whereby the pivotal movement of the jib arm about the joint is measured by an encoder which incorporates a compensator and is mounted to the joint with compensation of the relative movement of the pivot to the joint. This allows the encoder to detect the deflecting movement of the jib arm with the relative movement of the pivot to the joint compensated and thus locate the focal point correctly in the vertical direction.

2 Claims, 3 Drawing Sheets

DEFLECTION COMPENSATING STRUCTURE FOR MEDICAL STAND APPARATUS

BACKGROUND OF THE INVENTION

1. Field of the Invention

The present invention relates to a balancing stand apparatus arranged for advancing and holding a heavy device such as a medical optical device at a desired spatial position and particularly, provided with a plurality of encoders which are mounted to significant joints in the stand apparatus for monitoring the focal point of the medical optical device.

2. Prior Art

Microsurgery is known particularly in the fields of brain surgery and cardiac surgery in which used an operating microscope as a "medical optical device" for viewing and inspecting a part to be treated during the surgical operation. Various stand apparatuses are available for holding at a desired spatial location the operating microscope which is heavy (for example, as shown in Japanese Patent Laid-open Publication 56-32110 (1981)). A typical type of the stand apparatus comprises a retaining link mechanism of parallel link pivotally (or tiltably) mounted at the middle to a support base, an operating microscope mounted to one end of the retaining link mechanism, and a counterweight mounted to the other end of the retaining link mechanism for countervailing the weight of the operating microscope relative to the pivot thereof.

In addition, a number of systems have been developed in which encoders are mounted to corresponding joints (of pivotal points) of the stand apparatus for producing measurements which are used for calculating the focal point of the operating microscope. The calculated focal point is then displayed together with tomographic images of a CT, MRI, or other equivalent system.

Such conventional stand apparatuses allow the encoders mounted at the corresponding joints to monitor the focal point of the operating microscope but not accurately detect an error derived from "deflection" on the stand apparatus. If the parallel link assemblies and jib arm in the stand apparatus are rigid enough to produce "zero" of deflection, the encoders may correctly locate the focal point. The jib arm of the medical stand apparatus is however loaded at its distal end with the weight of the operating microscope (and its auxiliary devices if any) and thus deflects downwardly. As the result, the focal point of the operating microscope will be incorrectly located in the vertical direction.

The present invention is directed towards overcoming the disadvantage of the prior art and its object is to provide a deflection compensating structure for a medical stand apparatus capable of compensating for a deflection of the jib arm.

SUMMARY OF THE INVENTION

A deflection compensating mechanism for a medical stand apparatus according to the present invention is characterized by a compensating arm extending from the proximal end at the joint to the distal end of the jib arm and arranged identical in the horizontal length to the jib arm. The compensating arm is pivotally joined at its distal end to the distal end of the jib arm and at its proximal end fixedly joined to a pivot which extends across the joint of the jib arm so that the pivotal movement of the jib arm about the joint is measured by an encoder which incorporates a compensator and is mounted to the joint with the relative movement of the pivot to the joint compensated.

When the distal end of the jib arm is downwardly deflected by the weight of a medical optical device, the compensating arm deflects downwardly along with the jib arm. Being joined to the proximal end of the compensating arm extends across the joint of the jib arm without direct contact, the pivot rotates relative to the joint of the jib arm. This allows the encoder mounted to the joint to measure the pivotal movement of the jib arm about the joint with the relative movement of the pivot compensated and thus locate the focal point correctly in the vertical direction.

The present invention is not limited to the above description and its other objects, advantages, features, and applications will be more apparent from the following description in conjunction with the accompanying drawings. It should be understood that various changes and modifications are possible without departing from the scope and spirit of the present invention.

DESCRIPTION OF THE PREFERRED EMBODIMENT

Figure 1:
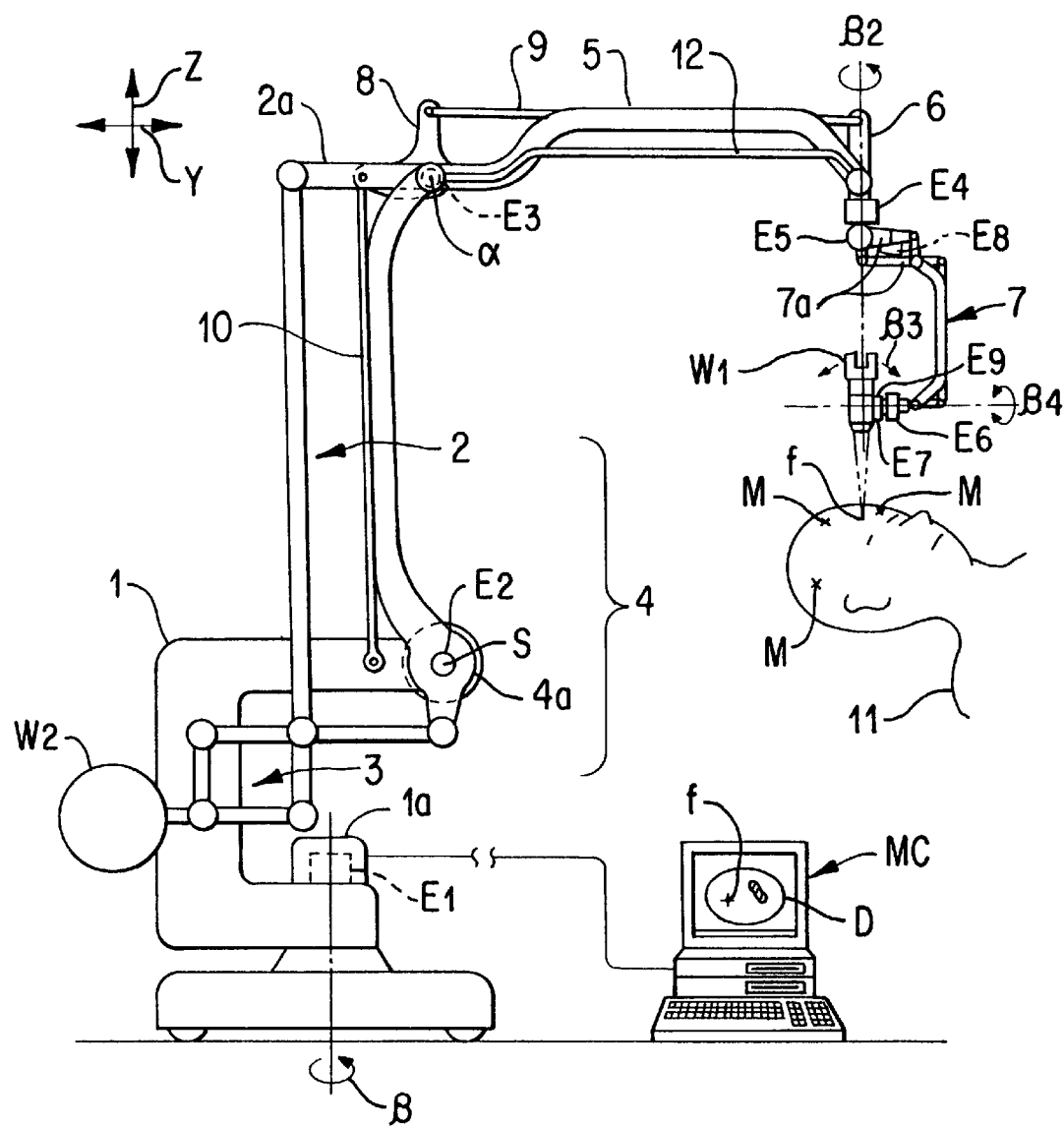
FIG. 1 is an overall side view of a medical stand apparatus according to the present invention.

A preferred embodiment of the present invention will be described in more details referring to FIGS. 1 to 4. For ease of the description, X represents leftward and rightward (FIG. 4), Y is forward and rearward, and Z upward and downward throughout the drawings.

A stand apparatus according to the present invention comprises a retaining link mechanism 4 composed of a first parallel link assembly 2 and a second parallel link assembly 3 and pivotally mounted at its part (middle 4a) to the center of pivot S of a mount base 1, an optical microscope (a medical optical device) $W_1$ mounted to the distal end of a jib arm 5 which extends forwardly from an upper horizontal arm 2a of the first parallel link assembly 2, and a counterweight $W_2$ mounted to the second parallel link assembly 3 for balancing the stand apparatus. The jib arm 5 has an arcuate shape setting back upwardly for clearing the head of a surgeon.

More specifically, the jib arm 5 has a vertically extending front arm 6 mounted to the distal end thereof. The front arm 6 is joined at the lower end with a parallel support link assembly 7 which comprises a pair of smaller parallel links. The operating microscope $W_1$ is held by the lower end of the parallel support link assembly 7 so that its viewing angle can be varied by the action of the parallel support link assembly 7.

An L-shaped crank member 8 is pivotally mounted at center to the proximal joint α of the jib arm 5. The L-shaped crank member 8 is joined at one end via a horizontal sub-arm 9 to the upper end of the front arm 6 and at the other end via a vertical sub-arm 10 to the mount base 1. This allows the crank member 8 to be held untiltable by the action of the horizontal and vertical sub-arms 9 and 10 even if the retaining link mechanism 4 is turned about the center pivot S. Accordingly, the front arm 6 remains vertical and the parallel support link assembly 7 to which the operating microscope $W_1$ is mounted does not tilt. Also, the second parallel link assembly 3 to which the counterweight $W_2$ is mounted for countervailing the weight of the operating microscope $W_1$ produces a balance and holds the operating microscope $W_1$ at a desired spatial position after released form a hand.

The stand apparatus of the embodiment also includes a number of encoders $E_1$ to $E_9$ mounted to the corresponding joints for monitoring the focal point f of the operating microscope $W_1$. The encoder $E_1$ is mounted to the swivel point 1a of the mount base 1 for measuring a pivotal movement about an axis B. The pivotal movement about the axis B by the encoder $E_1$ is indicative of a location of the focal point f in the X direction (See FIG. 4). As the mount base 1 with the retaining link mechanism 4 is swiveled about the axis B, the operating microscope $W_1$ travels leftward or rightward. Although, strictly speaking, the leftward or rightward movement of the operating microscope $W_1$ traces an arc, the movement may be considered a horizontal straight movement because such an arc is merely recognized through a microscope.

The encoder $E_2$ is mounted to the center pivot S for measuring the focal point f in the forward or rearward (Y). The encoder $E_3$ is mounted to the joint $\alpha$ of the jib arm 5 for measuring the focal point f in the upward or downward (Z). The latter acts as a primary part of the present invention and will be explained later in more details.

The encoders $E_4$ and $E_5$ are mounted to the parallel support link assembly 7 which is joined to the lower end of the vertical front arm 5. The encoder $E_4$ measures a pivotal movement about the axis $\beta_2$. The encoder $E_4$ is useful when the focal point f is displaced from the axis $\beta_2$ (inversely, the encoder $E_4$ is not used if the focal point f is aligned with $\beta_2$). The encoder $E_5$ detects a tilting of the operating microscope $W_1$ towards $\beta_3$ from a biasing movement of the parallel support link assembly 7 and determines a displacement of the focal point f in the Y direction in case that the parallel support link assembly 7 is positioned as illustrated.

The encoder $E_6$ measures a pivotal movement about the axis $\beta_4$. The encoder $E_7$ is of a linear model for measuring a vertical position of the operating microscope $W_1$. The upper horizontal arm 7a of the parallel support link assembly 7 is arranged variable in length. As the length of the upper horizontal arm 7a is varied, the operating microscope $W_1$ moves forward or backward in the Y direction. The encoder $E_8$ is also of a linear model for measuring a Y-directional movement of the operating microscope $W_1$. The encoder $E_9$ is mounted to the proximal end of the operating microscope $W_1$ for measuring a self-tilting of the operating microscope $W_1$ towards $\beta_3$.

Since the length of the jib arm 5 is fixed, the location of the focal point f of the operating microscope $W_1$ can be calculated from the pivotal movements and displacements measured by the encoders $E_1$ to $E_9$. Accordingly, it is favorable for ease of the surgical operation that the measurements of the encoder $E_1$ to $E_9$ are transferred to a microcomputer MC provided for displaying a tomographic image D of CT or MRI so that the focal point f is indicated as overlapped with the tomographic image D on a screen of the microcomputer MC. This permits the positional relation between the focal point f and a target (i.e. a part to be treated) in the tomographic image D to be clearly viewed.

In practice, three metallic markers M are attached to the head of a patient 11 and the focal point f of the operating microscope $W_1$ is located on each marker M to record their positions into the microcomputer MC which in turn calculates the origins (not shown) of the markers M. Then, the head with the markers M is tomographed and its tomograph D is examined to read the locations of the markers M indicated therein. When the locations read from the tomograph D are aligned with the origins recorded in the microcomputer MC, the focal point f on the screen defines the movement of the stand apparatus. This allows the surgeon to instantly acknowledge the location of the focal point f of the operating microscope $W_1$ on the head of the patient.

Figure 3:
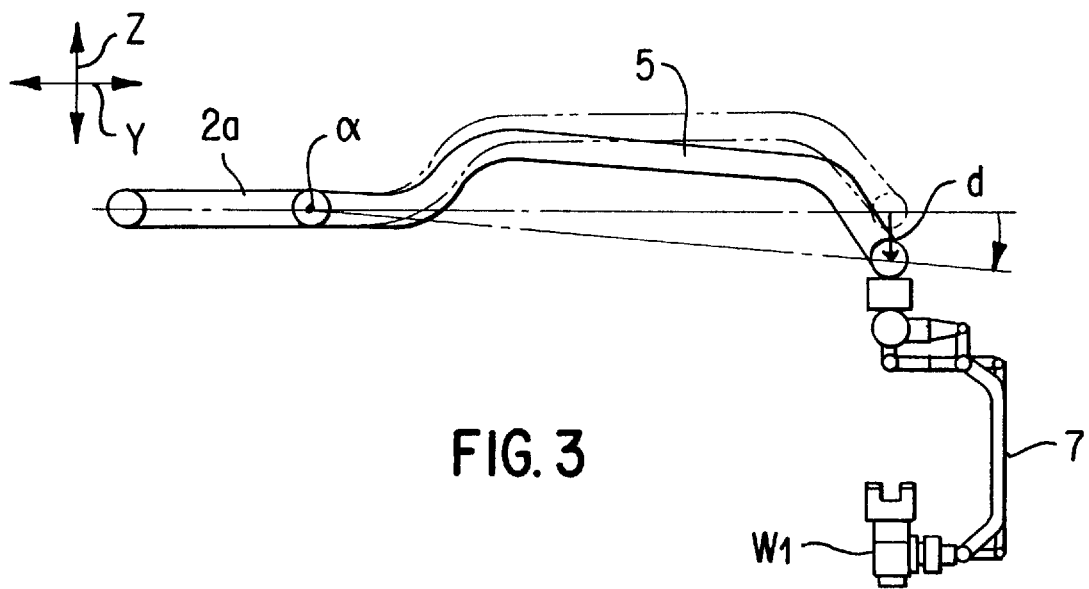
FIG. 3 is a side view of the jib arm carrying a medical optical device.
Figure 4:
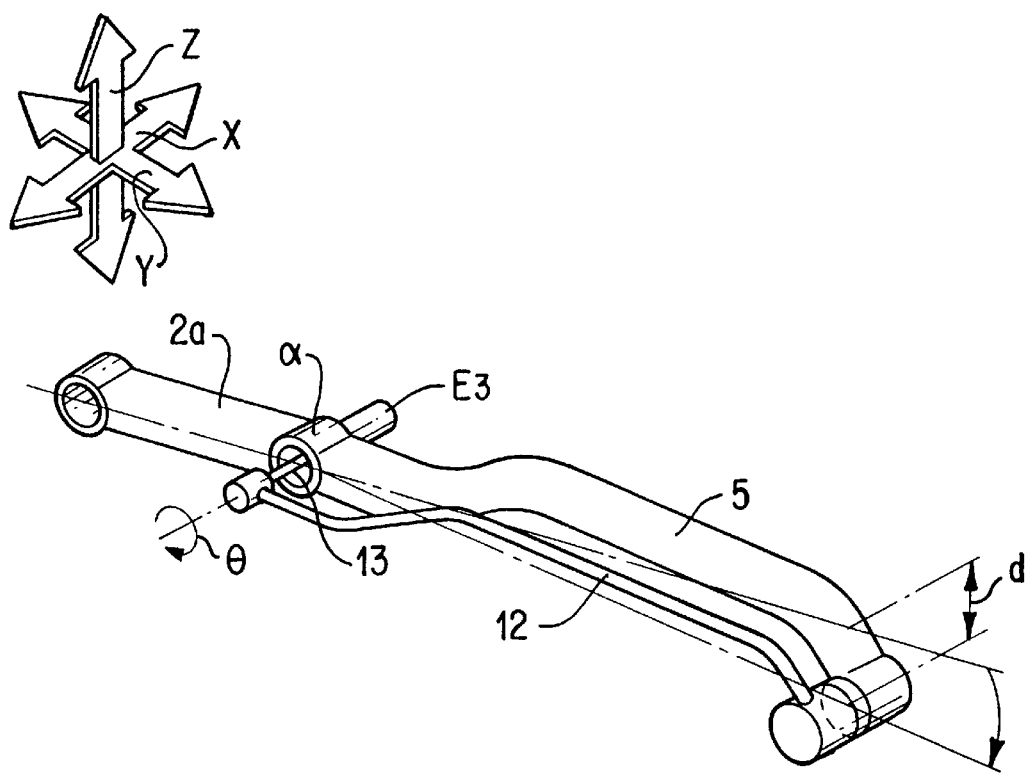
FIG. 4 is a perspective view showing a relation between the jib arm and a compensating arm.

The structural feature of the present invention will now be explained in detail referring to FIGS. 2 to 4. A compensating arm 12 is provided extending in parallel to and arranged identical in the horizontal length to the jib arm 5. The compensating arm 12 is slightly and upwardly curved like the jib support 5. The compensating arm 12 is pivotally supported at the front end to the front end of the jib arm 5. The rear or distal end of the compensating arm 12 is provided with a pivot 13 (FIG. 4) which extends across the joint $\alpha$ of the jib arm 5. The pivot 13 is linked to the encoder $E_3$ for measuring the pivotal movement of the jib arm 5 about the joint $\alpha$. The encoder $E_3$ hence detects the pivotal movement about the joint $\alpha$ of the jib arm 5 with the relative movement of the pivot 13 to the jib arm 5 compensated.

Figure 2:
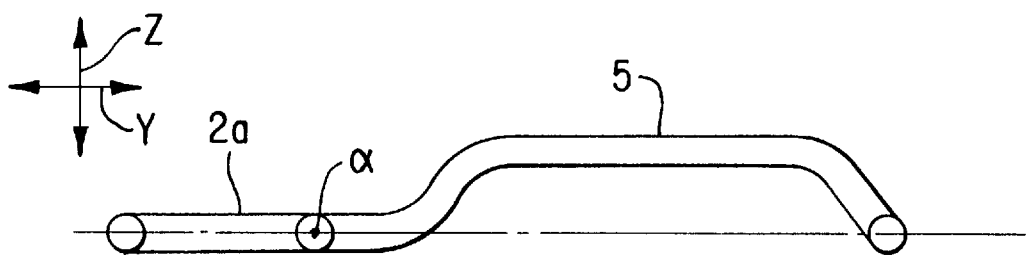
FIG. 2 is a side view of a jib arm carrying no medical optical device.

For example, the jib arm 5 extends horizontally with no downward deflection when the operating microscope $W_1$ is not loaded as shown in FIG. 2. However, the jib arm 5 when loaded with the operating microscope $W_1$ via the parallel support link assembly 7 is downwardly deflected at its front end by the weight of the operating microscope $W_1$ and its auxiliary devices if any. If the weight of the operating microscope $W_1$ causes the front end of the jib arm 5 to be downwardly deflected by a distance d, the compensating arm 12 joined to the jib arm 5 also deflects downward. As the front end of the compensating arm 12 deflects, the pivot 13 which extends across the joint $\alpha$ of the jib arm 5 without direct contact is downwardly rotated through $\theta$ in relation to the joint $\alpha$ of the jib arm 5. The encoder $E_3$ hence detects the pivotal movement of the jib arm 5 with the relative displacement of the pivot 13 compensated and allows the location of the focal point f to be correctly read in the vertical direction. In the embodiment, the focal point f of the operating microscope $W_1$ can precisely be measured in the vertical direction and displayed together with the tomographic image D on the screen. This allows the surgeon to correctly locate the target (i.e. a part to be treated) of the patient displayed in the tomograph D in relation to the focal point f of the operating microscope $W_1$.

As set forth above, the deflection compensating mechanism of the medical stand apparatus of the present invention allows the focal point of any medical optical device to be correctly located with the deflection compensated when the front end of the jib arm is downwardly deflected by the weight of the medical optical device. Accordingly, while its focal point is visually being indicated in a tomographic image on the screen, the medical optical device can be operated with higher accuracy and effectiveness.

What is claimed is:

1. A deflection compensating structure for a medical stand apparatus, comprising:
   a retaining link mechanism that includes:
      a first parallel link assembly having a first end and a second end, and
      a second parallel link assembly having a first end and a second end,
      the first parallel link and the second parallel link coupled to each other for movement as a linkage;
   a mount base having a pivot center, wherein the retaining link mechanism is pivotally mounted to the pivot center of the mount base;

a counterweight mounted to the first end of the second parallel link assembly for balancing a rotational moment about the pivot center;

a jib arm having a first end, a second end, and a jib arm joint, the jib arm extending at the first end of the jib arm from the first end of the first parallel link assembly;

a medical optical device mounted to the second end of the jib arm;

a compensating arm having a first end and a second end, the compensating arm pivotally joined at the second end of the compensating arm to the second end of the jib arm;

a pivot extending through the jib arm joint and joined to the compensating arm at the first end of the compensating arm allowing movement of the compensating arm relative to the jib arm joint;

a crank member having a first extension and a second extension attached to the pivot;

a first sub-arm with a first end and a second end, the first sub-arm first end attached to the first extension of the crank member and the first sub-arm second end attached to the jib arm second end;

a second sub-arm with a first end and a second end, the second sub-arm first end attached to the second extension of the crank member and the second sub-arm second end attached at the second end of the first parallel link assembly;

an encoder mounted to the jib arm joint, wherein the pivotal movement of the jib arm about the jib arm joint is measured by the encoder to allow compensation relative to the crank member, the pivotal movement of the crank member being prevented by the first sub-arm and the second sub-arm.

2. A deflection compensating structure for a medical stand apparatus according to claim 1, further comprising an encoder for measuring the focal point of the medical optical device mounted by a parallel support link assembly to the second end of the jib arm.

* * * * *